Jan. 15, 1974 D. L. ARMSTRONG Plant Pat. 3,440
ROSE PLANT
Filed March 8, 1972
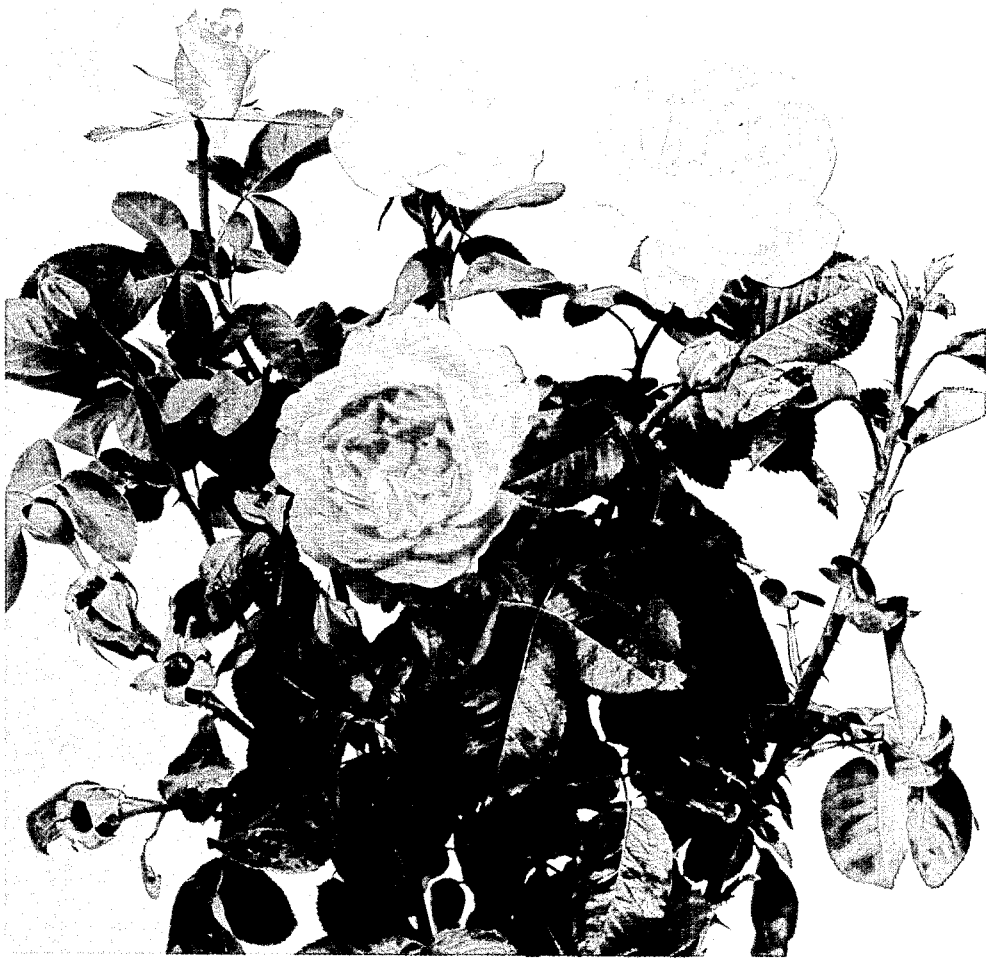

United States Patent Office

Plant Pat. 3,440
Patented Jan. 15, 1974

3,440
ROSE PLANT

David L. Armstrong, Upland, Calif., assignor to
Armstrong Nurseries, Inc., Ontario, Calif.
Filed Mar. 8, 1972, Ser. No. 232,984
Int. Cl. A01h 5/00
U.S. Cl. Plt.—11 1 Claim

ABSTRACT OF THE DISCLOSURE

A new variety of asexually reproduced grandiflora rose characterized primarily in the color transition of its bloom, from yellow overlaid with red as the calyx breaks, then through purplish red petals streaked with yellow, after which the petals of the cup-shaped bloom are progressively light yellow with some petals almost white and others sometimes tipped with purplish pink, then deepen to a purplish pink intermixed with yellow, and when full blown, the flower is purplish red with little if any yellow showing. The plant is of a very tall bush type with a tendency to develop pendant tips of the initial canes. The leaves are large, dark green and glossy, and leathery in texture. Initial primary stems tend to bear clusters of five or more flowers; on later growth there are some clusters of from five to two blooms, and occasionally a flower is borne singly.

This invention relates to a new variety of grandiflora rose, of the tall, bush type, grown as an outdoor seedling for cut flowers and garden decoration. It was propagated and grown in Ontario, Calif.

The plant is a seedling having as its seed parent Buccaneer (Plant Pat. No. 1,119) and as its pollen parent El Capitan (Plant Pat. No. 1,796). It holds its distinguishing characteristics through succeeding propagations by budding.

The accompanying drawing illustrates the plant in color and shows the flowering thereof from bud to full bloom.

This new variety may be distinguished from its seed parent, Buccaneer, in the following characteristics:

The plant of this new variety bears flowers with colors ranging from greenish yellow to near-white at the basal areas of the petals to shades of purplish-pink to purplish-red at the upper extremities of the petals, whereas the flowers of Buccaneer are buttercup yellow, with little or no variation. The buds of this new cultivar give the overall effect of pink, whereas the buds of Buccaneer are rich yellow, occasionally marked slightly with red.

The flowers of Buccaneer range from 3" to 3½" in diameter, with 30 petals, whereas this new cultivar has a flower diameter of from 3¼" to 4¼", with 25 to 30 petals, plus 6 to 12 petaloids.

The Buccaneer peduncles have numerous gland-tipped cilia and a few very small prickles, but this new cultivar has not only numerous stipitate glands but also numerous small prickles on its peduncles.

The leaves of Buccaneer are similar to but somewhat smaller in size and lighter green in color than in this new cultivar. Also, there are characteristically fewer and smaller prickles on the rachis of the leaves of Buccaneer than are to be found on the back of the rachis of this new cultivar.

Whereas Buccaneer usually bears its flowers singly, and only occasionally three or more to a stem, this new cultivar bears its initial flowers at the end of long primary canes in clusters of usually five or more to a stem. It does also bear later a single flower to a stem in addition to clusters, but such clusters as it does produce characteristically contain substantially more flowers than the clusters of Buccaneer.

This new variety is distinguished from its pollen parent, El Capitan, in the following respects:

This new cultivar, although equally upright and tall, is not as bushy as El Capitan and tends to have much longer primary canes, which often become somewhat pendant when they produce their characteristically large clusters of flowers.

Whereas the leaves of El Capitan are relatively small and flat, the leaves of this new variety are quite large, particularly with respect to the terminal and last two marginal leaflets.

While the prickles on the back of the rachis of El Capitan have a similar character to those of this new cultivar, they are substantially smaller and usually less numerous.

Whereas the flowers of El Capitan are cherry to rose-red in color, the flowers of this new cultivar are predominantly pink with some basal variation in the yellow and near white range.

The flowers of this new variety are sometimes borne singly but usually in irregular clusters of two to five, or more, to a stem, on normal, medium stems. The plant blooms abundantly outdoors, and nearly continuously during the growing season. The fragrance is moderate tea.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is average length, of average to heavy caliper, and may be bending or erect. Its color is near Strong Yellow Green, 5GY 6/8, overlaid where exposed to sunlight with near Dark Red, 2.5R 3/7. It bears numerous stipitate glands and numerous small prickles.

Before the calyx breaks, the bud is medium to large in size, pointed and ovoid.

As the calyx breaks, the color is between Brilliant Yellow, 5Y 9/9, and Brilliant Yellow Green, 2.5GY 8/9, overlaid with near Strong Red, 5R 4/12, where exposed to sunlight.

A fine wooly tomentum lines the inner surface of the sepals and the margins of alternate sepals. The margins of the other sepals have numerous stipitate glands and small foliaceous appendages. The tips of the sepals sometimes have foliaceous parts extending beyond the tip a distance of usually not more than one-half the bud length. There usually are stipitate glands on the outer surface.

As the first petal opens, it is average to large in size, of medium length, and ovoid to urn-shaped. The outer surface of the petal is between Strong Greenish Yellow, 10Y 8/11, and Brilliant Greenish Yellow, 10Y 9/9, lightly to heavily overlaid as exposed to light, with between Strong Purplish Red, 10RP 4/12, and Strong Purplish Red, 7.5RP 5/12. The inner surface of the petal is between Vivid Greenish Yellow, 7.5Y 8/12, and Brilliant Greenish Yellow, 7.5Y 9/8, overlaid lightly to heavily in spots with between Strong Purplish Pink, 7.5RP 7/10, and Strong Purplish Red, 10RP 4/12.

The bud opens up well and is not retarded or prevented from opening by cold, hot, or dry weather.

BLOOM

When fully open, the bloom is average in size, being from 3¼" to 4½" in diameter. The petalage is double, with from 25 to 30 petals, plus 6 to 12 petaloids arranged irregularly.

The form of the bloom is cupped at first, becoming open to cupped later. At first, the petals remain somewhat tightly cupped, with tips rolled outward. Later, at maturity, they become somewhat more loosely cupped, with tips still rolled outward.

The petals are of medium thickness, moderately leathery, with both inside and outside slightly shiny to satiny.

Both outside and intermediate petals are obovate in shape. The inside petals are also obovate, but sometimes irregular, and sometimes with one or more notches. Their colors may be modified by being bordered, shaded and/or washed with other colors.

The following description applies to a newly opened flower grown outdoors in the month of October, in Ontario, Calif.:

The outer surface of the outside petal is near Vivid Greenish Yellow, 7.5Y 8/12, at the base near the point of attachment, becoming lighter than Brilliant Greenish Yellow, 7.5Y 9/8, overlaid with a color ranging from Strong Purplish Pink, 7.5RP 7/10, to between Strong Purplish Red, 7.5RP 4/11, and Strong Purplish Red, 10RP 4/12, being darker where the petal had more exposure to sunlight. The inner surface of the outside petal is near Vivid Greenish Yellow, 7.5Y 8/12, at the base, becoming lighter than Brilliant Greenish Yellow, 7.5Y 9/8 overlaid lightly nearer the middle and more heavily near the margins with between Deep Purplish Pink, 7.5RP 6/12, and Strong Purplish Red, 7.5RP 5/12, sometimes with a darker spot near the apex between Strong Purplish Red, 7.5RP 4/11, and Deep Purplish Red, 10RP 3/10.

The outer surface of the intermediate petal is near Vivid Greenish Yellow, 7.5Y 8/12, near the base, becoming near Brilliant Greenish Yellow, 7.5Y 9/8, or lighter, towards the margin. It is lightly overlaid near its margin with near Light Purplish Pink, 7.5RP 8/5. The inside surface of the intermediate petal is near Vivid Greenish Yellow, 7.5Y 8/12, at the base, becoming near Brilliant Greenish Yellow, 7.5Y 9/8, or lighter, towards the margin. It is lightly overlaid near the margin with near Light Purplish Pink, 7.5RP 8/5.

The outer surface of the inner petal is near Vivid Greenish Yellow, 7.5Y 8/12, at the base, becoming near Brilliant Greenish Yellow, 7.5Y 9/8, or lighter, towards the margin, very faintly overlaid with near Light Purplish Pink, 7.5RP 8/5, near the margin. The inside surface of the inner petal was of the same coloration as the outer surface.

The description which follows was made from a rose that was open for three days outdoors in the month of October, in Ontario, Calif.:

The outer surface of the outside petal is near Brilliant Greenish Yellow, 7.5Y 9/8, at the base, fading to near white away from the base, and overlaid with between Strong Purplish Red, 7.5RP 5/12, and Strong Purplish Red, 7.5RP 4/11, where exposed to light as the bud opened. The inner surface of the outside petal is near Brilliant Greenish Yellow, 7.5Y 9/8, at the base, fading to near white away from the base, and overlaid with between Strong Purplish Red, 7.5RP 5/12, and Moderate Red, 2.5R 4/10, according to exposure to sunlight.

The outer surface of the inside petal is near Brilliant Greenish Yellow, 7.5Y 9/8, at the base, becoming near white throughout the petal, lightly overlaid from mid-petal to margins with between Deep Purplish Pink, 7.5RP 6/12, and Strong Purplish Red, 7.5RP 5/12. The inside surface of the inside petal is near Brilliant Greenish Yellow, 7.5Y 9/8, near the base, becoming near-white where shaded and generously overlaid where exposed to sunlight with between Strong Purplish Red, 7.5RP 5/12, and Strong Purplish Red, 10RP 4/12.

The general color effect of the newly opened flower is lighter than, but between Brilliant Greenish Yellow, 7.5Y 9/8, and Brilliant Yellow, 5Y 9/9, lightly blushed along the outside circumference with near Light Purplish Pink, 7.5RP 8/5. After the bloom has been three days open, the color effect is more vivid than, but between Strong Purplish Red, 10RP 5/12, and Strong Purplish Red, 10RP 4/12.

The petals usually drop off cleanly, and are not particularly affected by cold, hot, wet, or dry weather.

In Southern California, the flower persists on the bush in the garden from four to five days, or more, in the month of October. Roses grown outdoors, but cut and kept at living room temperatures, persist from four to six days in the month of October.

*Reproductive organs*

Stamens: The stamens are average in number, arranged irregularly about the pistils, a few being mixed pith petaloids, or sometimes tucked in the calyx.

Filaments: The filaments are medium in length, from 4 to 15 mm. Their color is near Brilliant Greenish Yellow, 10Y 9/9. Most are with anthers.

Anthers: The anthers are medium in size, opening at various times. On both the upper side and the under side the color is near Brilliant Greenish Yellow, 10Y 9/9. Just before opening, the margins are near Moderate Orange Yellow, 10YR 8/10.

Pollen: The pollen is moderate in quantity, and near Strong Orange Yellow, 7.5YR 7/11, in color.

Pistils: The pistils are average in number, there being approximately 70 of them.

Styles: The styles are moderately even, average in length and caliper, and somewhat loosely bunched. Their color is near Brilliant Greenish Yellow, 10Y 9/9, overlaid near the stigma with near Strong Purplish Red, 10RP 5/12.

Stigma: The stigma is near Moderate Orange Yellow, 10YR 8/10, in color.

Ovaries: The ovaries are, for the most part, enclosed in the calyx.

Hips: The hips are average in length, ovoid to globular. At half maturity, the color is between Strong Yellow Green, 2.5GY 6/8, and Moderate Yellow Green, 2.5GY 5/5. They are moderately smooth, with fleshy walls, and sometimes with a few to many stipitate glands.

Sepals: The sepals are permanent until fully mature, medium-length, and either straight or recurved. Their inside color, when the hips are at half maturity, is near Light Olive Brown, 2.5Y 5/5, but with more gray because of tomentum, while the outside color is near Strong Yellow Green, 5GY 6/8, with many stipitate glands.

Seeds: Seeds are few to average in number, from four to ten, and are usually medium in size.

FOLIAGE

The compound leaves usually comprises from 3 to 7 leaflets, and are from normal to abundant. They are medium size to large, moderately heavy to somewhat leathery, and semi-glossy. The leaflets are oval to obovoid in shape, with apex acute, base obtuse, and margin simply to doubly serrate.

The color of the mature foliage on the uppersurface is near Moderate Olive Green, 5GY 4/3, when grown outdoor. The under surface is more gray than a color near Moderate Yellow Green, 2.5GY 5/5, when grown outdoors.

The young growth, on its upper surface is near Moderate Yellow Green, 5GY 5/6, heavily overlaid with near Dark Red, 2.5R 3/7. The under surface is near Strong Yellow Green, 5GY 6/8, heavily overlaid with near Dark, Red, 2.5R 3/7.

The rachis is average to heavy in size, grooved, and with many stipitate glands on the edges. The upper side is prickly, with stipitate glands.

The stipules are long and medium-length, being moderately narrow to medium-width, and with medium-length points turning out at an angle of more than 45°.

The plant is mildly subject to mildew, when grown outdoors in Ontario, Calif.

GROWTH

The plant is bushy, upright, much to moderately branched, with tips somewhat pendant. Its growth is very vigorous, and the canes are from medium caliper to heavy.

The main stems are between Strong Yellow Green, 2.5GY 6/8, and Moderate Yellow Green, 2.5GY 5/5. They bear several large prickles which are medium-length to long, hooked slightly downward, with medium-length to long, moderately narrow base. The large prickles are between Brownish Orange, 5YR 5/8, and Moderate Reddish Brown, 2.5YR 3/3. There are many small prickles which are the same color as the large prickles. There are no hairs, but several stipitate glands.

The branches are between Moderate Yellow Green, 5GY 5/6, and Strong Yellow Green, 5GY 6/8. There are few to several large prickles which are medium-length to long, hooked slightly downward, with medium-length, moderately narrow base. These large prickles are from near Brilliant Yellow, 2.5Y 9/9, overlaid with near Moderate Red, 2.5R 4/10, to near Moderate Reddish Brown, 2.5YR 3/3. There are from very few to many small prickles, and these are the same color as the large prickles. There are no hairs, but from few to many stipitate glands.

New shoots are between Strong Yellow Green, 5GY 6/8, and Moderate Yellow Green, 5GY 5/6, lightly to heavily overlaid with near Dark Red, 2.5R 3/7, on the side exposed to sunlight. There are few to several large prickles, medium-length to long, hooked slightly downward, with medium-length moderately narrow base. Their color is near Strong Yellow Green, 2.5GY 6/8, lightly to very heavily overlaid with near Dark Red, 2.5R 3/7.

There are from few to many small prickles whose coloring is the same as that of the large prickles. There are no hairs, but from few to many stipitate glands.

I claim:

1. A new variety of asexually reproduced rose plant of the grandiflora class, substantially as herein illustrated and described, said plant being characterized by a plurality of combinations of features, including tall height for the Grandiflora class, large dark green leaves of leathery and glossy texture, blooms grouped usually in clusters of five or more flowers, particularly on the initial primary stems, with numerous smaller clusters on later growth, and only occasionally a single bloom; the petals numbering from about 25 to about 30 and there being from 6 to 12 petaloids and about 70 pistils, the ovaries being mostly enclosed within the calyx; the new variety being especially characterized by color transition of the bloom, the petals being red touched with yellow as the calyx breaks, becoming purplish red color with yellow near the base as the bud opens, then forming a cup-shaped bloom which reveals buttercup yellow petalage in its center, thereafter becoming purplish pink, and finally distinctly purplish red with little if any of the yellow color showing on the face of the bloom.

No references cited.

ROBERT E. BAGWILL, Primary Examiner